(12) United States Patent
Hoang et al.

(10) Patent No.: US 10,406,343 B2
(45) Date of Patent: *Sep. 10, 2019

(54) PATIENT FLUID LINE ACCESS VALVE ANTIMICROBIAL CAP/CLEANER

(71) Applicant: Becton, Dickinson and Company, Franklin Lakes, NJ (US)

(72) Inventors: Minh Quang Hoang, Sandy, UT (US); Jonathan Karl Burkholz, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/697,060

(22) Filed: Sep. 6, 2017

(65) Prior Publication Data
US 2018/0043148 A1    Feb. 15, 2018

Related U.S. Application Data

(63) Continuation of application No. 15/041,939, filed on Feb. 11, 2016, which is a continuation of application (Continued)

(51) Int. Cl.
*A61M 39/16* (2006.01)
*A61M 39/02* (2006.01)
(Continued)

(52) U.S. Cl.
CPC .......... *A61M 39/162* (2013.01); *A61M 39/02* (2013.01); *A61M 39/16* (2013.01);
(Continued)

(58) Field of Classification Search
CPC .... A61M 39/16; A61M 39/20; A61M 39/162; A61M 39/165
See application file for complete search history.

(56) References Cited

U.S. PATENT DOCUMENTS

| 2,961,682 A | 11/1960 | Wurmbock et al. |
| 3,047,139 A | 7/1962 | Jacoff |

(Continued)

FOREIGN PATENT DOCUMENTS

| EP | 1 649 890 A1 | 4/2006 |
| EP | 2606930 A1 | 6/2013 |

(Continued)

OTHER PUBLICATIONS

"Corrected Petition for Inter Partes Review Under 35 U.S.C. §§ 311-319 and 37 C.F.R. § 42,100 et seq.," USPTO, Patent Trial and Appeal Board, Excelsior Medical Corporation v. Becton, Dickinson and Company, Case IPR2014-00880, U.S. Pat. No. 8,740,864, pp. 1-48, dated Jun. 23, 2014.

(Continued)

*Primary Examiner* — Andrew Gilbert
(74) *Attorney, Agent, or Firm* — Dickinson Wright, PLLC

(57) ABSTRACT

Cap and cleaning devices antiseptically maintain patient fluid line access valves to minimize the risk of infection via catheters. The devices have a cap that may contain a dry pad impregnated with an antimicrobial agent. The cap covers the access portion of the access valve when not in use. The devices have a hood that contains a wet pad impregnated with a cleaning solution and, optionally, an antimicrobial agent. The wet pad cleans the access portion of the access valve prior to and optionally, after the access valve is utilized to access the patient fluid line.

21 Claims, 7 Drawing Sheets

Related U.S. Application Data

No. 14/159,959, filed on Jan. 21, 2014, now Pat. No. 9,283,367, which is a continuation of application No. 11/281,711, filed on Nov. 17, 2005, now Pat. No. 8,740,864.

(51) Int. Cl.
*A61M 39/20* (2006.01)
*A61M 39/04* (2006.01)
*A61M 39/10* (2006.01)

(52) U.S. Cl.
CPC .......... *A61M 39/20* (2013.01); *A61M 39/045* (2013.01); *A61M 2039/1033* (2013.01); *A61M 2039/1072* (2013.01); *Y10T 137/4259* (2015.04)

(56) References Cited

U.S. PATENT DOCUMENTS

| | | |
|---|---|---|
| 3,136,416 A | 6/1964 | Goldrosen |
| 3,147,876 A | 9/1964 | Lepore |
| 4,280,632 A | 7/1981 | Yuhara |
| 4,282,891 A | 8/1981 | Duceppe |
| 4,354,490 A | 10/1982 | Rogers |
| 4,417,890 A | 11/1983 | Dennehey et al. |
| 4,432,764 A | 2/1984 | Lopez |
| 4,440,207 A * | 4/1984 | Genatempo ............ A61L 31/16 150/154 |
| 4,444,310 A | 4/1984 | Odell |
| 4,584,192 A | 4/1986 | Dell et al. |
| 4,624,664 A | 11/1986 | Peluso et al. |
| 4,626,664 A | 12/1986 | Grise |
| 4,655,762 A | 4/1987 | Rogers |
| 4,671,306 A | 6/1987 | Spector |
| 4,716,032 A | 12/1987 | Westfall et al. |
| 4,778,447 A * | 10/1988 | Velde .................... A61M 39/10 604/29 |
| 4,915,934 A | 4/1990 | Tomlinson |
| 4,925,668 A | 5/1990 | Khan et al. |
| 4,989,733 A | 2/1991 | Patry |
| 4,991,629 A | 2/1991 | Ernesto et al. |
| 5,006,114 A | 4/1991 | Rogers et al. |
| 5,023,082 A | 6/1991 | Friedman et al. |
| 5,195,957 A | 3/1993 | Tollini |
| 5,197,620 A | 3/1993 | Gregory |
| 5,242,425 A * | 9/1993 | White .................... A61M 39/20 604/256 |
| 5,334,388 A | 8/1994 | Hoang et al. |
| 5,335,373 A | 8/1994 | Dangman et al. |
| 5,512,199 A | 4/1996 | Khan et al. |
| 5,547,662 A | 8/1996 | Khan et al. |
| 5,554,106 A | 9/1996 | Layman-Sipllar et al. |
| 5,554,135 A * | 9/1996 | Menyhay ............ A61M 39/162 138/89 |
| 5,569,207 A | 10/1996 | Gisselberg et al. |
| 5,616,338 A | 4/1997 | Fox, Jr. et al. |
| 5,620,424 A | 4/1997 | Abramson |
| 5,639,310 A | 6/1997 | Giampaolo, Jr. |
| 5,641,464 A | 6/1997 | Briggs, III et al. |
| 5,686,096 A | 11/1997 | Khan et al. |
| 5,694,978 A * | 12/1997 | Heilmann ............ A61M 39/20 138/103 |
| 5,702,017 A | 12/1997 | Goncalves |
| 5,706,944 A | 1/1998 | Hoang et al. |
| 5,722,537 A | 3/1998 | Sigler |
| 5,743,884 A | 4/1998 | Hasson et al. |
| 5,792,120 A | 8/1998 | Menyhay |
| 5,817,344 A | 10/1998 | Hoang et al. |
| 5,861,440 A | 1/1999 | Gohla et al. |
| D410,081 S | 5/1999 | Sweeney et al. |
| 5,954,957 A | 9/1999 | Chin-Loy et al. |
| 5,989,229 A | 11/1999 | Chiappella |
| 6,045,539 A | 4/2000 | Menyhay |
| 6,051,609 A | 4/2000 | Yu et al. |
| 6,074,366 A | 6/2000 | Rogers et al. |
| 6,116,468 A | 9/2000 | Nilson |
| 6,117,114 A * | 9/2000 | Paradis ............... A61M 39/045 604/246 |
| 6,146,360 A | 11/2000 | Rogers et al. |
| 6,196,998 B1 | 3/2001 | Jansen et al. |
| 6,227,391 B1 | 5/2001 | King |
| 6,337,357 B1 | 1/2002 | Fukunishi et al. |
| 6,413,539 B1 | 7/2002 | Shalaby |
| 6,416,496 B1 | 7/2002 | Rogers et al. |
| 6,482,188 B1 | 11/2002 | Rogers et al. |
| 6,488,942 B1 | 12/2002 | Ingemann |
| 6,523,686 B1 | 2/2003 | Bae |
| RE38,145 E | 6/2003 | Lynn |
| 6,664,893 B1 | 12/2003 | Eveland et al. |
| 6,665,385 B2 | 12/2003 | Rogers et al. |
| 6,708,363 B2 | 3/2004 | Larsen |
| 6,846,846 B2 | 1/2005 | Modak et al. |
| 6,861,060 B1 | 3/2005 | Luriya et al. |
| 6,911,025 B2 | 6/2005 | Miyahara |
| 6,957,107 B2 | 10/2005 | Rogers et al. |
| 6,979,323 B2 | 12/2005 | Rogers et al. |
| 6,994,315 B2 | 2/2006 | Ryan et al. |
| 7,002,468 B2 | 2/2006 | Eveland et al. |
| 7,130,396 B2 | 2/2006 | Rogers et al. |
| 7,083,605 B2 | 8/2006 | Miyahara |
| 7,198,611 B2 | 4/2007 | Connell et al. |
| 7,198,800 B1 | 4/2007 | Ko |
| 7,268,165 B2 | 9/2007 | Greten et al. |
| 7,282,186 B2 | 10/2007 | Lake, Jr. et al. |
| 7,452,349 B2 | 11/2008 | Miyahara |
| D607,325 S | 1/2010 | Rogers et al. |
| 7,682,561 B2 | 3/2010 | Davis et al. |
| 7,704,002 B2 | 4/2010 | Fisher et al. |
| 7,704,935 B1 | 4/2010 | Davis et al. |
| 7,780,794 B2 | 8/2010 | Rogers et al. |
| 7,828,186 B2 | 11/2010 | Wales |
| 7,857,793 B2 | 12/2010 | Raulerson et al. |
| 7,922,701 B2 | 4/2011 | Buchman |
| 7,985,302 B2 | 7/2011 | Rogers et al. |
| 7,993,309 B2 | 8/2011 | Schweikert |
| 8,065,773 B2 | 11/2011 | Vaillancourt et al. |
| 8,069,523 B2 | 12/2011 | Vaillancourt et al. |
| 8,113,731 B2 | 2/2012 | Cable et al. |
| 8,162,899 B2 | 4/2012 | Tennican |
| 8,167,847 B2 | 5/2012 | Anderson et al. |
| 8,172,825 B2 | 5/2012 | Solomon et al. |
| 8,177,761 B2 | 5/2012 | Howlett et al. |
| 8,197,749 B2 | 6/2012 | Howlett et al. |
| 8,206,514 B2 | 6/2012 | Rogers et al. |
| 8,231,587 B2 | 7/2012 | Solomon et al. |
| 8,273,303 B2 | 9/2012 | Ferlic et al. |
| 8,290,129 B2 | 10/2012 | Rogers et al. |
| 8,328,767 B2 | 12/2012 | Solomon et al. |
| 8,336,151 B2 | 12/2012 | Kerr et al. |
| 8,336,152 B2 | 12/2012 | Vaillancourt et al. |
| 8,343,112 B2 | 1/2013 | Solomon et al. |
| 8,388,894 B2 | 3/2013 | Colantonio et al. |
| 8,419,713 B1 | 4/2013 | Solomon et al. |
| 8,491,546 B2 * | 7/2013 | Hoang .................. A61M 39/02 604/267 |
| 8,506,538 B2 | 8/2013 | Chelak |
| 8,523,830 B2 | 9/2013 | Solomon et al. |
| 8,523,831 B2 | 9/2013 | Solomon et al. |
| 8,628,501 B2 | 1/2014 | Hadden |
| 8,641,681 B2 | 2/2014 | Solomon et al. |
| 8,647,308 B2 | 2/2014 | Solomon et al. |
| 8,647,326 B2 | 2/2014 | Solomon et al. |
| 8,671,496 B2 | 3/2014 | Vaillancourt et al. |
| 8,696,820 B2 | 4/2014 | Vaillancourt et al. |
| 8,721,627 B2 | 5/2014 | Alpert |
| 8,740,864 B2 * | 6/2014 | Hoang .................. A61M 39/02 604/267 |
| 8,777,504 B2 | 7/2014 | Shaw et al. |
| 8,789,713 B2 | 7/2014 | Koller |
| 8,808,637 B2 | 8/2014 | Ferlic |
| 8,828,327 B2 | 9/2014 | Colantonio et al. |
| 8,832,894 B2 | 9/2014 | Rogers et al. |
| 8,834,650 B2 | 9/2014 | Rogers et al. |

(56) References Cited

U.S. PATENT DOCUMENTS

| | | |
|---|---|---|
| 8,845,593 B2 | 9/2014 | Anderson et al. |
| 8,961,475 B2 | 2/2015 | Solomon et al. |
| 8,968,268 B2 | 3/2015 | Anderson et al. |
| 8,999,073 B2 | 4/2015 | Rogers et al. |
| 9,101,750 B2 | 8/2015 | Solomon et al. |
| 9,259,535 B2 | 2/2016 | Anderson et al. |
| 9,283,367 B2 * | 3/2016 | Hoang .............. A61M 39/02 |
| 9,283,368 B2 * | 3/2016 | Hoang .............. A61M 39/02 |
| 2001/0016589 A1 | 8/2001 | Modak et al. |
| 2002/0144705 A1 | 10/2002 | Brattesani et al. |
| 2003/0040708 A1 | 2/2003 | Rogers et al. |
| 2003/0072781 A1 | 4/2003 | Pelerin |
| 2003/0109853 A1 | 6/2003 | Harding et al. |
| 2003/0153865 A1 | 8/2003 | Connell et al. |
| 2003/0162839 A1 | 8/2003 | Symington et al. |
| 2004/0004019 A1 * | 1/2004 | Busch .............. A61B 17/3401 206/571 |
| 2004/0039349 A1 | 2/2004 | Modak et al. |
| 2004/0073171 A1 | 4/2004 | Rogers et al. |
| 2004/0258560 A1 | 12/2004 | Lake, Jr. et al. |
| 2005/0124970 A1 | 6/2005 | Kunin et al. |
| 2005/0147524 A1 | 7/2005 | Bousquet |
| 2005/0147525 A1 | 7/2005 | Bousquet |
| 2005/0165351 A1 | 7/2005 | Tamagni, Jr. |
| 2006/0030827 A1 | 2/2006 | Raulerson et al. |
| 2006/0165751 A1 | 7/2006 | Chudzik et al. |
| 2006/0239954 A1 | 10/2006 | Sancho |
| 2007/0112333 A1 | 5/2007 | Hoang et al. |
| 2007/0202177 A1 | 8/2007 | Hoang |
| 2007/0225660 A1 | 9/2007 | Lynn |
| 2007/0282280 A1 | 12/2007 | Tennican |
| 2008/0027399 A1 | 1/2008 | Harding et al. |
| 2008/0033371 A1 | 2/2008 | Updegraff et al. |
| 2008/0075761 A1 | 3/2008 | Modak et al. |
| 2008/0086091 A1 * | 4/2008 | Anderson .......... A61M 5/31511 604/192 |
| 2008/0095680 A1 | 4/2008 | Steffens et al. |
| 2008/0147047 A1 | 6/2008 | Davis et al. |
| 2008/0177250 A1 | 7/2008 | Howlett et al. |
| 2008/0182921 A1 | 7/2008 | Suh et al. |
| 2008/0283534 A1 | 11/2008 | Paz |
| 2009/0008393 A1 | 1/2009 | Howlett et al. |
| 2009/0028750 A1 | 1/2009 | Ryan |
| 2009/0028756 A1 | 1/2009 | Shahriari |
| 2009/0062766 A1 | 3/2009 | Howlett et al. |
| 2009/0149819 A1 * | 6/2009 | Chelak .............. A61M 39/162 604/246 |
| 2009/0175759 A1 | 7/2009 | Davis et al. |
| 2010/0000040 A1 | 1/2010 | Shaw et al. |
| 2010/0047123 A1 | 2/2010 | Solomon et al. |
| 2010/0049170 A1 | 2/2010 | Solomon et al. |
| 2010/0050351 A1 | 3/2010 | Colantonio et al. |
| 2010/0172794 A1 * | 7/2010 | Ferlic .............. A61L 2/238 422/28 |
| 2010/0204648 A1 | 8/2010 | Stout et al. |
| 2010/0292673 A1 | 11/2010 | Korogi et al. |
| 2010/0306938 A1 | 12/2010 | Rogers et al. |
| 2011/0150958 A1 | 6/2011 | Davis et al. |
| 2011/0232020 A1 | 9/2011 | Rogers et al. |
| 2011/0265825 A1 | 11/2011 | Rogers et al. |
| 2011/0290799 A1 * | 12/2011 | Anderson .......... A61M 5/31511 220/200 |
| 2011/0314619 A1 | 12/2011 | Schweikert |
| 2012/0016318 A1 | 1/2012 | Hoang et al. |
| 2012/0039765 A1 | 2/2012 | Solomon et al. |
| 2012/0078203 A1 | 3/2012 | Gaube et al. |
| 2012/0216359 A1 | 8/2012 | Rogers et al. |
| 2012/0216360 A1 * | 8/2012 | Rogers .............. A61B 19/34 15/104.93 |
| 2012/0283693 A1 | 11/2012 | Anderson et al. |
| 2012/0315201 A1 | 12/2012 | Ferlic et al. |
| 2013/0030414 A1 | 1/2013 | Gardner et al. |
| 2013/0072909 A1 | 3/2013 | Solomon et al. |
| 2013/0136801 A1 | 5/2013 | Tennican |
| 2013/0138083 A1 | 5/2013 | Tennican |
| 2013/0138085 A1 | 5/2013 | Tennican |
| 2013/0171030 A1 | 7/2013 | Ferlic et al. |
| 2013/0199947 A1 | 8/2013 | Tennican |
| 2013/0270270 A1 | 10/2013 | Reinders |
| 2013/0335195 A1 | 12/2013 | Rogers |
| 2013/0345645 A1 | 12/2013 | Chelak |
| 2014/0135739 A1 | 5/2014 | Solomon et al. |
| 2014/0150832 A1 | 6/2014 | Rogers et al. |
| 2014/0182623 A1 | 7/2014 | Vaillancourt et al. |
| 2014/0188089 A1 | 7/2014 | Midgelle et al. |
| 2014/0248181 A1 | 9/2014 | Solomon et al. |
| 2014/0248182 A1 | 9/2014 | Solomon et al. |
| 2014/0261558 A1 | 9/2014 | Rogers et al. |
| 2014/0261581 A1 | 9/2014 | Rogers |
| 2014/0366914 A1 | 12/2014 | Kerr et al. |
| 2015/0018774 A1 | 1/2015 | Anderson et al. |
| 2015/0086441 A1 | 3/2015 | She et al. |
| 2015/0094694 A1 | 4/2015 | Stone et al. |
| 2015/0217106 A1 | 8/2015 | Banik et al. |
| 2015/0273199 A1 | 10/2015 | Adams et al. |
| 2015/0314119 A1 | 11/2015 | Anderson et al. |
| 2015/0314120 A1 | 11/2015 | Gardner |
| 2016/0015959 A1 | 1/2016 | Solomon et al. |
| 2016/0074648 A1 | 3/2016 | Kerr et al. |
| 2016/0325089 A1 | 11/2016 | Burkholz |

FOREIGN PATENT DOCUMENTS

| | | |
|---|---|---|
| JP | S-58-501359 A | 8/1983 |
| JP | 2001-258713 A | 9/2001 |
| JP | 2009-511181 A | 3/2009 |
| JP | 2010-516342 A | 5/2010 |
| JP | 5867703 B2 | 2/2016 |
| WO | 97/00441 | 1/1987 |
| WO | 99/29173 | 6/1999 |
| WO | 2006/019782 A2 | 2/2006 |
| WO | 2007/044760 A2 | 4/2007 |
| WO | 2007/137056 A2 | 11/2007 |
| WO | 2008/100950 A2 | 8/2008 |
| WO | 2008/157092 A1 | 12/2008 |
| WO | 2010/039171 A1 | 4/2010 |
| WO | 2010/143693 A1 | 12/2010 |
| WO | WO-2010141508 A1 | 12/2010 |
| WO | 2011/053924 A1 | 5/2011 |
| WO | 2011/066586 A1 | 6/2011 |
| WO | 2015044904 A1 | 4/2015 |

OTHER PUBLICATIONS

"Patent Owner's Preliminary Response Under 37 C.F.R. § 42,10," USPTO, Patent Trial and Appeal Board, Excelsior Medical Corporation v. Becton, Dickinson and Company, Case IPR2014-00880, U.S. Pat. No. 8,740,864, pp. 1-30, dated Sep. 16, 2014.

"Decision, Institution of Inter Partes Review, 37 C.F.R. § 42,108," USPTO, Patent Trial and Appeal Board, Excelsior Medical Corporation v. Becton, Dickinson and Company, Case IPR2014-00880, U.S. Pat. No. 8,740,864, pp. 1-21, dated Nov. 25, 2014.

3M Health Care, "3M Curos Jet Disinfecting Cap Video," YouTube, Nov. 21, 2016, 1:12, 1:21-1:34. www.youtube.com/watch?v=MiUNz7lmuK4.

* cited by examiner

PATIENT FLUID LINE ACCESS VALVE ANTIMICROBIAL CAP/CLEANER

RELATED APPLICATIONS

This application is a continuation of U.S. application Ser. No. 15/041,939, filed Feb. 11, 2016, which is a continuation of U.S. application Ser. No. 14/159,959, filed Jan. 21, 2014, titled PATIENT FLUID LINE ACCESS VALVE ANTIMICROBIAL CAP/CLEANER, granted on Mar. 15, 2016 as U.S. Pat. No. 9,283,367, which is a continuation of U.S. application Ser. No. 11/281,711, filed Nov. 17, 2005, titled PATIENT FLUID LINE ACCESS VALVE ANTIMICROBIAL CAP/CLEANER, granted on Jun. 3, 2014 as U.S. Pat. No. 8,740,864 which are incorporated herein in their entirety.

BACKGROUND OF THE INVENTION

Catheter-related bloodstream infections are caused by bacteria/fungi in patients with intravascular catheters. These infections are an important cause of illness and excess medical costs, as approximately 80,000 catheter-related bloodstream infections occur in U.S. intensive care units each year. In addition to the monetary costs, these infections are associated with anywhere from 2,400 to 20,000 deaths per year.

Guidelines from the Centers for Disease Control and Prevention describe various ways to limit catheter-related bloodstream infections in hospital, outpatient and home care settings. The guidelines address issues such as hand hygiene, catheter site care and admixture preparation. Despite these guidelines, 15 catheter-related bloodstream infections continue to plague our healthcare system.

Impregnating catheters with various antimicrobial agents is one approach that has been implemented to prevent these infections. These catheters, however, have given less than satisfactory results. In addition, some microbes have developed resistance to the various antimicrobial agents in the system.

In another system that is commercially available in Europe, a catheter hub containing an antiseptic chamber is filled with three percent iodinated alcohol. Though it has shown to be effective, the catheter hub is expensive and does not fare as well in a formal cost-benefit analysis. Therefore, there is a need for an effective and inexpensive way to reduce the number of catheter-related infections.

BRIEF SUMMARY OF THE INVENTION

The present invention is a device for antiseptically maintaining a patient fluid line access valve. The device includes a housing for covering the access portion of the access valve. A pad within the housing contacts the surface of the access portion of the access valve prior to (and optionally after) accessing the patient fluid line via the access valve to reduce the amount of microbes on the valve's access portion.

DETAILED DESCRIPTION

Figure 1:
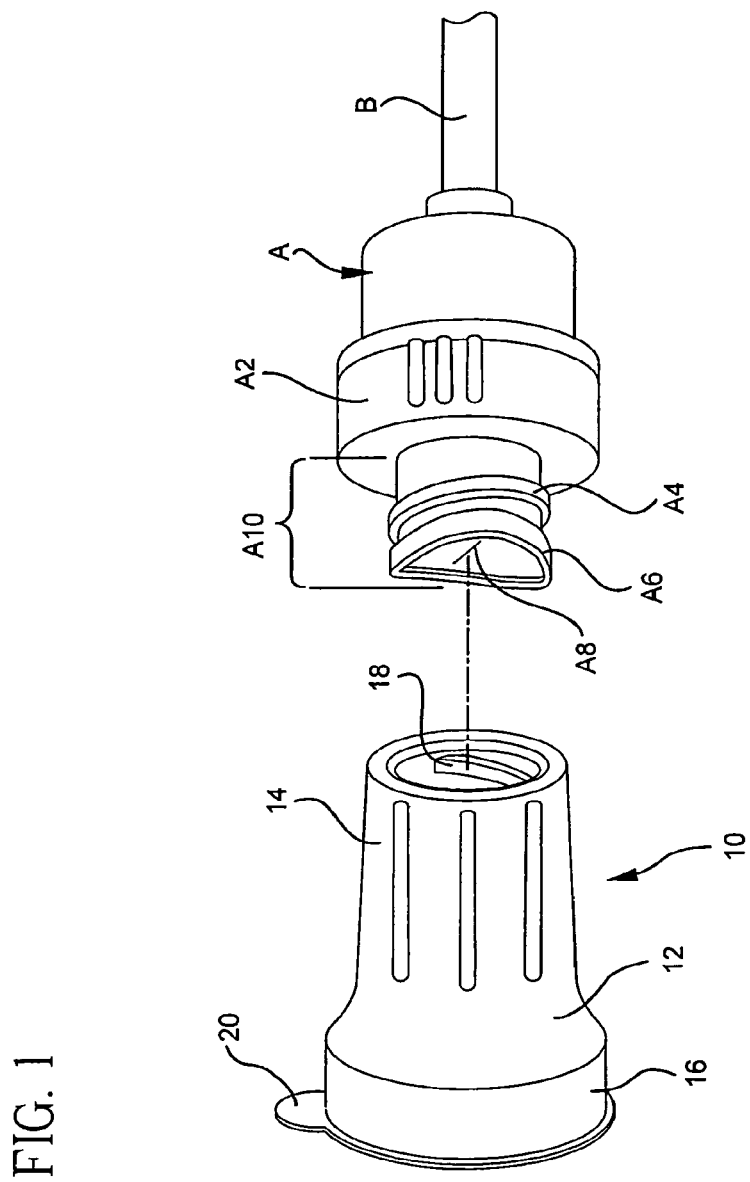
FIG. 1 is an exploded view of a first representative embodiment of a cap/cleaner device and a patient fluid line access valve.

FIG. 1 shows an exploded view of patient fluid line access valve cap/cleaner device 10 with patient fluid line access valve A and patient fluid line B. Cap/cleaner 10 includes housing 12 with cap end 14, cleaning end 16 and thread 18; and lid 20. Access valve A includes housing A2 with thread A4 and septum A6 with slit A8. The exposed surface of septum A6 A10*ng* with at least a portion of the exposed surface of housing A2 that surrounds septum A6, form access portion A10 of access valve A. Line B may be any of a number of types that include, for example, intravascular (IV) lines and catheters, saline wells, arterial lines and hemodialysis lines.

As will be described in more detail below, cap end 14 of cap/cleaner 10 attaches to access portion A10 of access valve A. Housing 12 is made from any of a number of types of plastic materials such as polycarbonate, polypropylene, polyethylene, glycol-modified polyethylene terephthalate, acrylonitrile butadiene styrene or any other moldable plastic material used in medical devices.

Cap end 14 of housing 12 is open and contains thread 18 A10*ng* the inside of the opening. Cleaning end 16 is covered by lid 20. Lid 20 is typically made of foil or similar type material and completely seals the opening (not shown) of cleaning end 16. Any type of material or seal may be used as long as a moisture barrier is provided.

Figure 2:
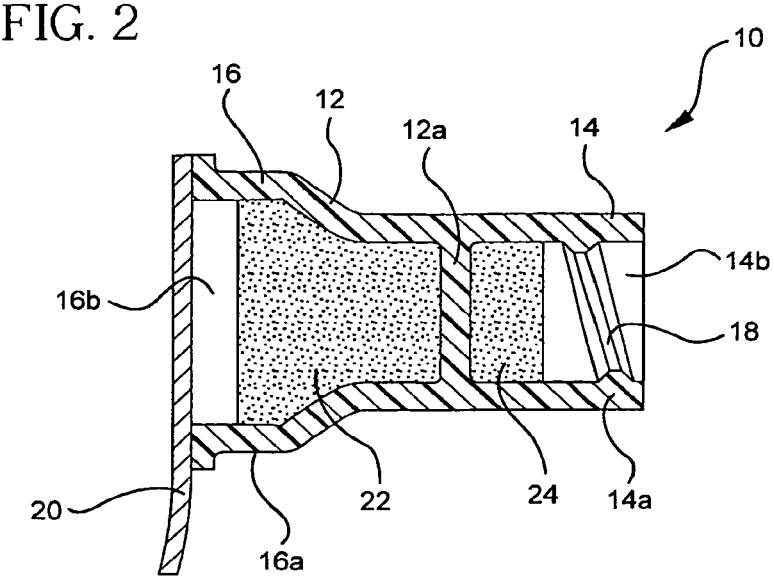
FIG. 2 is a cross-sectional side view of the first representative embodiment of the cap/cleaner device.

FIG. 2 shows cap/cleaner 10 in more detail. In addition to the structures shown in FIG. 1, cap/cleaner 10 also includes internal wall 12*a*, hood 16*a* and chamber 16*b* of cleaning end 16, cap 14*a* and cavity 14*b* of cap end 14, wet pad 22 within chamber 16*b* and dry pad 24 within cavity 14*b*. Internal wall 12*a* separates cap end 14 and cleaning end 16.

Cap/cleaner 10 is typically distributed and stored in a sterile, sealed package either A10*ne* or paired with a patient fluid line access valve. One such type of valve is the BD Q-Syte™ valve from Becton, Dickinson and Company (illustrated in FIG. 1). However, cap/cleaner 10 is useful with any type of needleless or needle required access valve. Once removed from the package, cap/cleaner 10 is ready for use.

Figure 3:
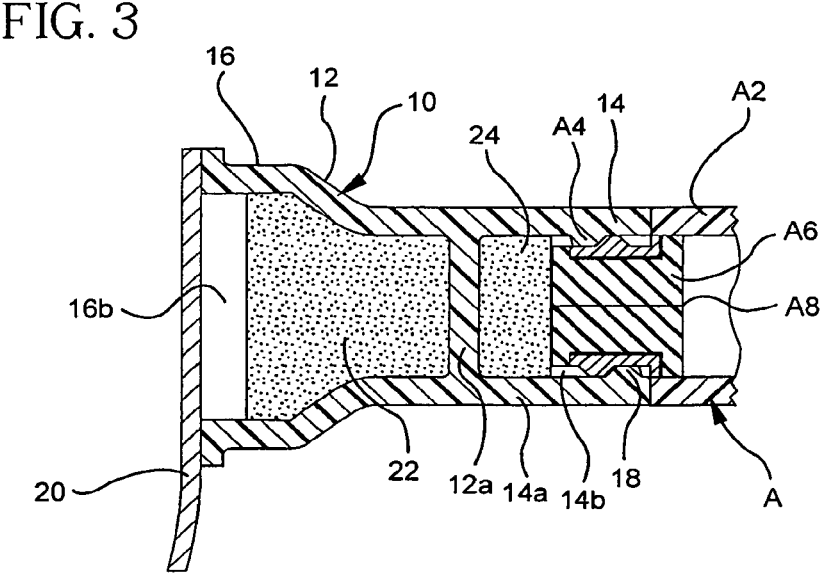
FIG. 3 is a cross-sectional side view of the first cap/cleaner device capping a patient fluid line access valve.

FIG. 3 illustrates cap/cleaner 10 covering access portion A10 of access valve A. Septum A6 provides an accessible seal for either a needle or a male luer taper. In the case of a needleless access device, such as that shown in FIG. 3, slit A8 extends through septum A6 to provide a port for insertion of the male luer taper.

As shown, cap end 14 includes cap 14*a* with cavity 14*b*, which contains dry pad 24. Dry pad 24 is impregnated with an antimicrobial agent to aid in maintaining antiseptic conditions of access portion A10 of valve A. Suitable material for dry pad 24 includes non-woven material or a foam sponge pad made of polyurethane, polyester, cotton or any bioengineered plastic material such as silicone. Any of a number of antimicrobial agents may be used to impregnate dry pad 24. Some examples include chlorhexidine gluconate, chlorhexidine diacetate, chloroxylenol, povidone iodine, Triclosan, benzethonium chloride, benzalkonium chloride, octenidine, antibiotic, etc. Alternatively, cap end 14 does not contain dry pad 24 and aids in maintaining antiseptic conditions by simply covering access portion A10.

In use, cap end 14 of cap/cleaner 10 is placed over access portion A10 such that access portion A10 is within cavity 14*b* of cap end 14. Cap/cleaner 10 may be attached either prior to or after placement of valve A for the patient. As shown in FIG. 3, valve A includes thread A4. By rotating cap/cleaner 10 or valve A relative to one another, threads A4 and 18 (of cap/cleaner 10) interlock to provide a secured attachment. It is not necessary, however, for valve A to include thread A4. Cap end 14 will also attach and hold a luer slip, which does not have a thread. In other embodiments, cap/cleaner 10 may be manufactured without a thread.

The amount of material used for dry pad 24 can vary. Typically, there is enough material for dry pad 24 to contact at least septum A6 of valve A. Enough space should be left in cavity 14*b* of cap end 14 for access portion A10 of valve A to be encompassed by cap end 14, thus, maintaining antiseptic conditions of the surface. By maintaining antiseptic conditions of the surface, the risk of microbes penetrating into valve A is minimized.

Figure 4:
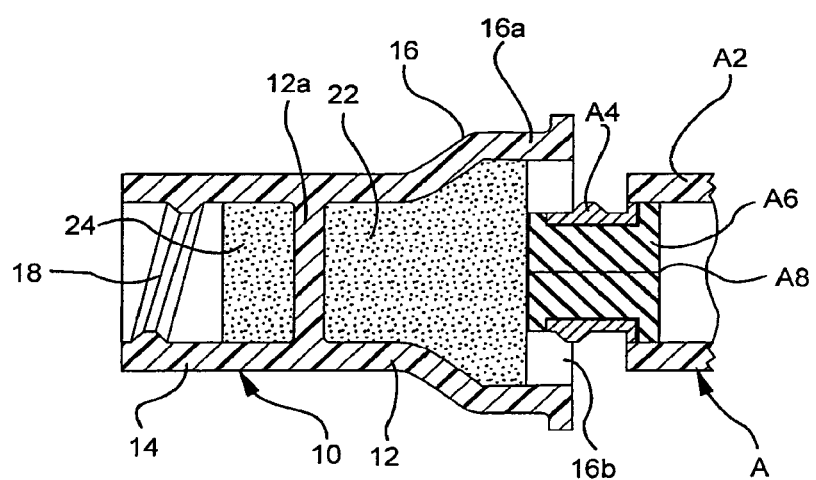
FIG. 4 is a cross-sectional side view of the first cap/cleaner device cleaning a patient fluid line access valve.

To further minimize the opportunity for penetration by microbes, access portion A10 is cleaned prior to accessing valve A with a needle or male luer taper. FIG. 4 illustrates cap/cleaner 10 cleaning access portion A10 of valve A.

As shown in FIG. 4, cleaning end 16 includes hood 16*a* and chamber 16*b*, which contains wet pad 22. Wet pad 22 is impregnated with a cleaning agent and optionally, an antimicrobial agent. Wet pad 22 may be made from materials similar to those described for dry pad 24.

The cleaning solution is typically an alcohol- or water-based solution. A suitable alcohol-based solution contains about 50% to about 100% (no additional water) of an alcohol solution. The balance of solutions that are less than 100% alcohol contain water and other optional materials such as fragrance, dye, surfactant, emollient, etc.

Suitable water-based solutions contain about 1% to about 10% alcohol solvent as a wetting agent and about 90% to about 99% water. Again, optional materials may also be added such fragrance, dye, surfactant, emollient, etc.

In an alternative embodiment, the cleaning solution also includes an antimicrobial agent. Any of a number of antimicrobial agents may be used in wet pad 22. Some examples include chlorhexidine gluconate, chlorhexidine diacetate, chloroxylenol, povidone iodine, Triclosan, benzethonium chloride, benzalkonium chloride, octenidine, antibiotic, etc. Wet pad 22 and dry pad 24 may be impregnated with the same or different antimicrobial agents.

As shown in the Figures, cleaning end 16 is larger than cap end 14. The hood of cleaning end 16 loosely encompasses at least access portion A10 of valve A, and chamber 16*b* is sized to allow some movement when access portion A10 is inserted. The amount of material used for wet pad 22 will vary, but the amount should hold enough cleaning solution and allow enough movement for thorough cleaning. Wet pad 22 should be contained entirely within hood 16*a* such that it is recessed inside chamber 16*b* of cleaning end 16.

In preparation for accessing valve A, cap end 14 is removed from valve A either by rotating cap/cleaner 10 to release threads 18 and A4 or by simply pulling if valve A does not have a thread. Lid 20 is removed from cleaning end 16. Cleaning end 16 is then placed over at least access portion A10, such that wet pad 22 contacts septum A6. Though FIG. 4 only shows contact with septum A6, additional pressure may be applied such that wet pad 22 extends beyond the edges of septum A6 to contact portions of the exposed surface of housing A2.

Next, for thorough cleaning, wet pad 22 should scrub access portion A10 of valve A. Scrubbing may be accomplished by, for example, rotational movement or back and forth movement. Scrubbing should be carried out for a time long enough to allow the cleaning solution to at least disinfect access portion A10 of valve A.

Once cleaned, valve A is ready to use. A needle or male luer taper is inserted to either infuse or withdraw fluid from the patient fluid line.

Figure 5:
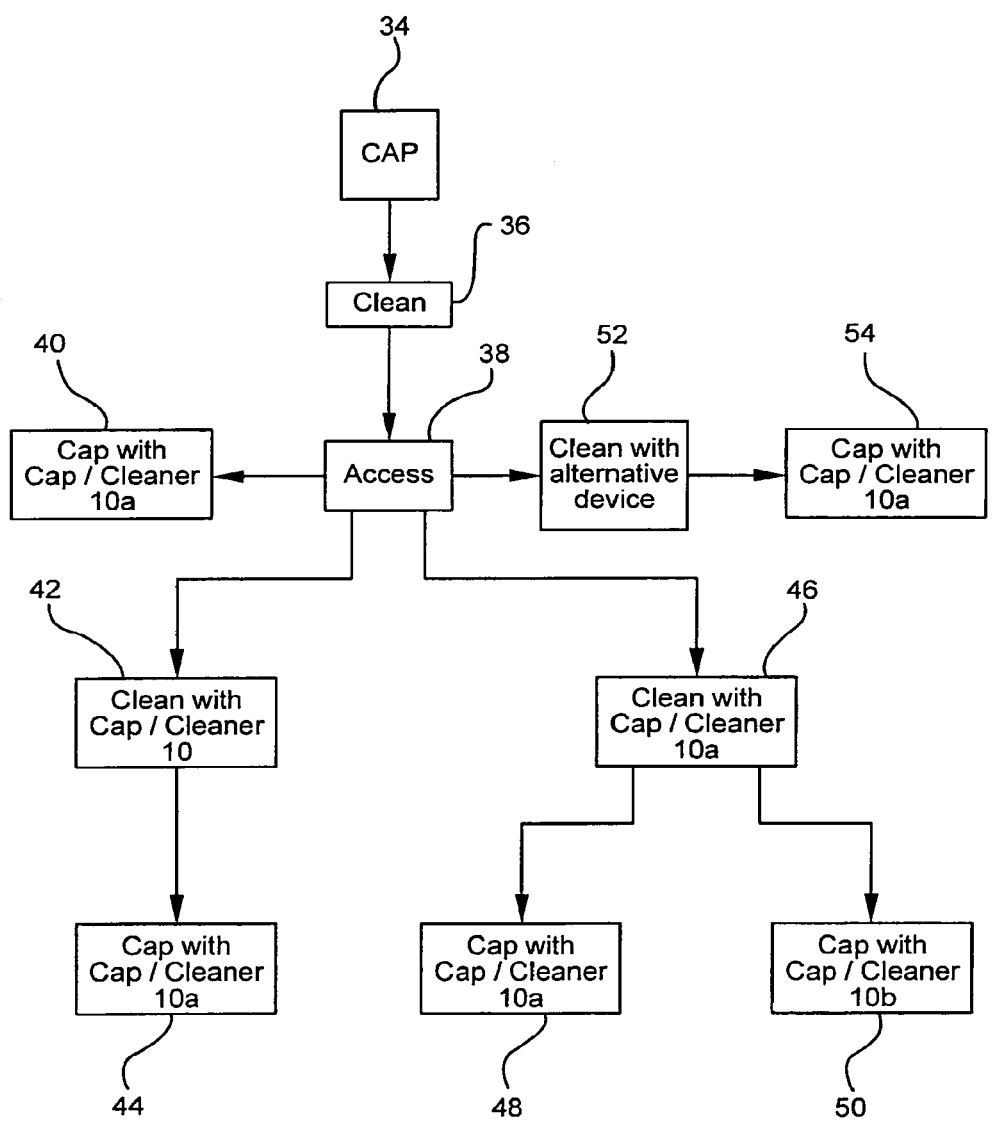
FIG. 5 is a flow chart illustrating representative embodiments of methods of using the cap/cleaner device.

FIG. 5 is a flowchart illustrating representative embodiments of methods for using cap/cleaner 10. Capping step 34, cleaning step 36 and accessing step 38 were described above and are the same in each embodiment. However, upon withdrawal after accessing the patient fluid line, access portion A10 of valve A may either be immediately capped or cleaned again prior to capping. If immediately capped, a new, second cap/cleaner 10A is obtained and removed from its package. This is represented by step 40. Cap end 14 of cap/cleaner 10A is placed over access portion A10 as described above. Cleaning end 16 of cap/cleaner 10A is sealed and ready for the next time valve A is utilized.

Alternatively, access portion A10 may be cleaned again prior to capping. This can be performed in one of the following ways. First, in step 42, cleaning end 16 of cap/cleaner 10 is reused to clean access portion A10, which is then capped, at step 44, with cap end 14 of a new, second cap/cleaner 10A. Second, in step 46, cleaning end 16 of a new, second cap/cleaner 10A is used to clean access portion A10. Then, valve A maybe capped either with cap end 14 of cap/cleaner 10A (step 48) or of a new, third cap/cleaner 10B (step 50). Third, in step 52, access portion A10 may be cleaned with an alternative disposable cleaning device that is well known in the art. Examples of such cleaning devices include alcohol wipes, iodine swabs, etc. Once cleaned, cap end 14 of a new, second cap/cleaner 10A may be attached to valve 26 (step 50).

Figure 6:
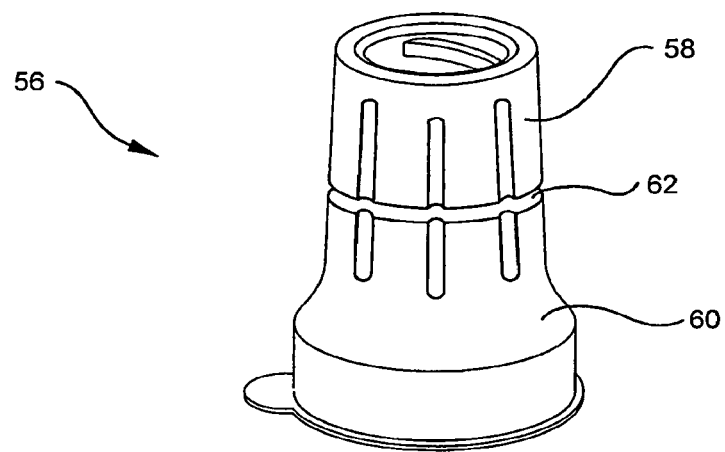
FIG. 6 is a perspective view of a second representative embodiment of a cap/cleaner device.

Additional embodiments of the present invention include separable and individual, uncoupled devices. FIG. 6 shows separable cap/cleaner 56. Separable cap/cleaner 56 includes cap end 58, cleaning end 60 and gap 62. Gap 62 is the separation between cap end 58 and cleaning end 60.

Figure 7:
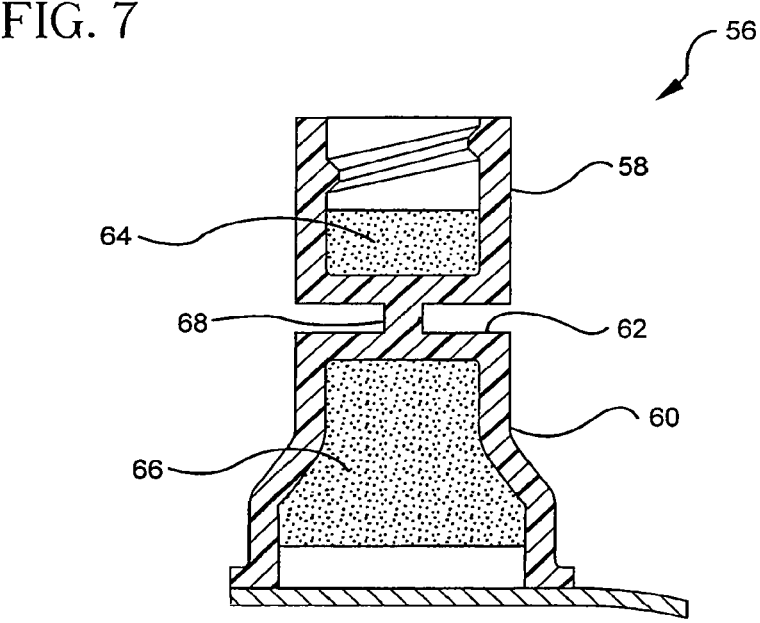
FIG. 7 is a cross-sectional side view of the second cap/cleaner device.

FIG. 7 shows separable cap/cleaner 56 in more detail and further includes dry pad 64 within cap end 58, wet pad 66 within cleaning end 60 and breakable connector 68. In use, separable cap/cleaner 56 operates as described above for 10 cap/cleaner 10 except that cleaning end 60 may be removed after cleaning access portion A10 of valve A. Detaching cleaning end 60 reduces bulkiness from separable cap/cleaner 56 by only maintaining cap end 58 over access portion A10.

Figure 8:
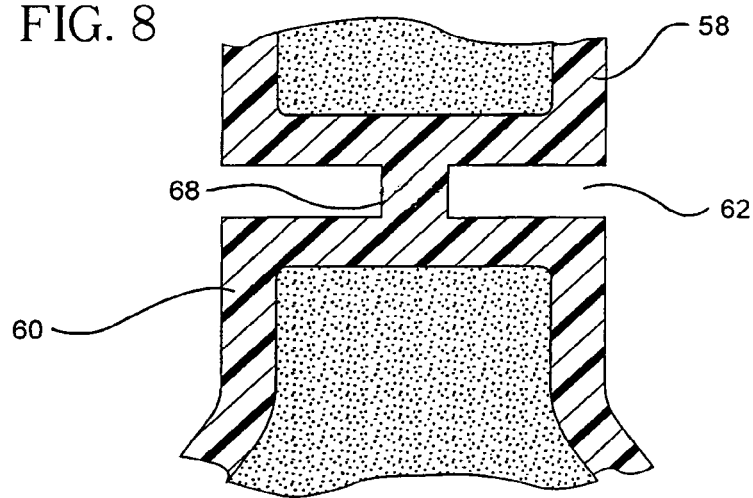
FIG. 8 is a cross-sectional view of a first separable connector.

FIG. 8 shows a representative embodiment of breakable connector 68. Connector 68 is typically made of the same material from which housing 12 is fabricated. Torsional shearing caused by twisting cap end 58 and/or cleaning end 60 relative to each other may be used to break connector. Alternatively, a three-point bending force, which consists of a fulcrum (connector 68) that directs a force vector contralateral to the direction of the terminal (cap end 58 and cleaning end 60) force vectors, may be applied for breaking connector 68. Once removed, cleaning end 60 may be discarded.

Figure 9:
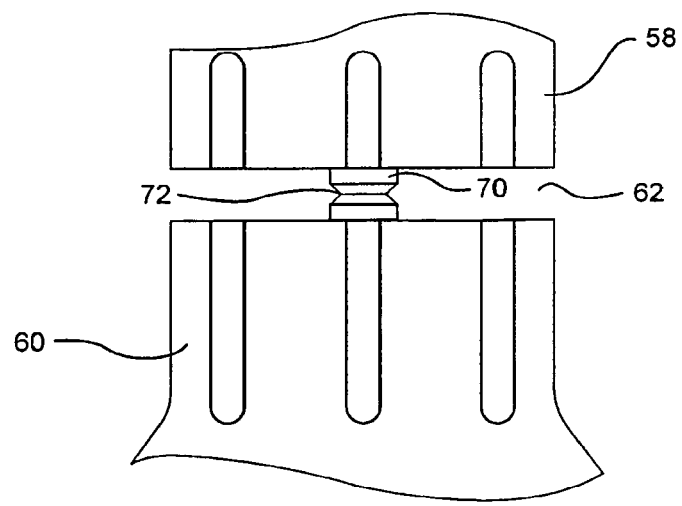
FIG. 9 is a side view of a second separable connector.

FIG. 9 is an alternate embodiment showing notched breakable connector 70. Notch 72 within connector 70 is an area of reduced cross-sectional area, which acts as a score to facilitate breaking of connector 70.

Other separation mechanisms may also be used to remove cleaning end 60 from cap end 58. For instance, a luer lock type mechanism can be utilized to separate ends 58 and 60 from each other.

Figure 10A:
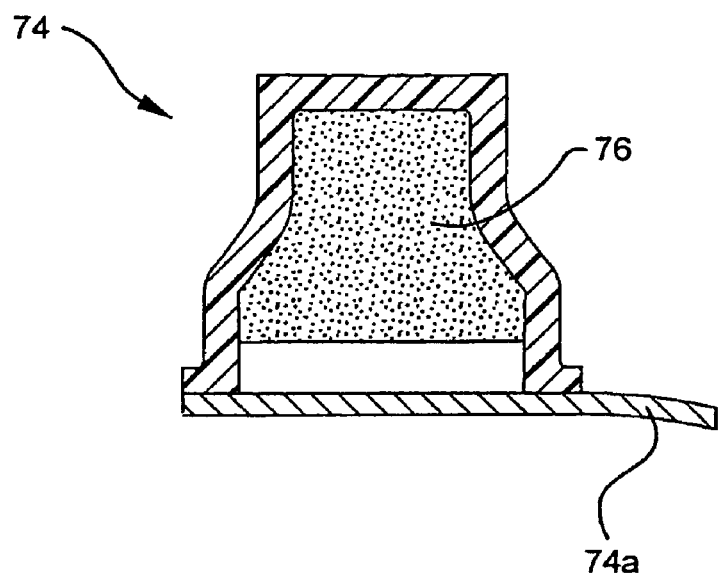
FIG. 10A is a cross-sectional view of cleaning device.

FIG. 10A shows a representative embodiment of cleaning device 74 with lid 74a and wet pad 76. Here, cleaning device 74 is a stand-alone device that is used as described above for cleaning end 16.

Figure 10B:
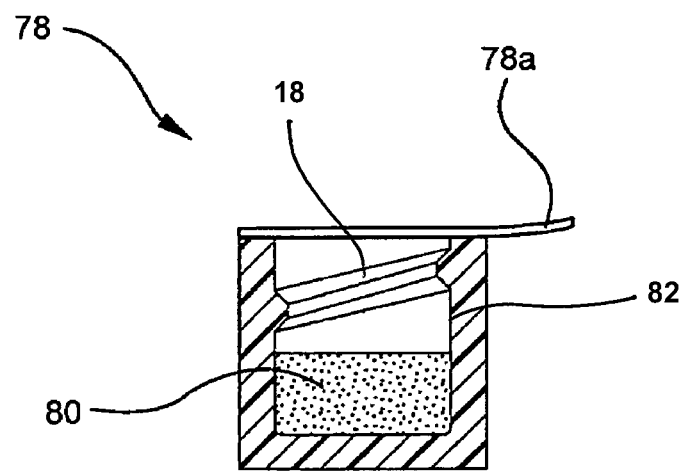
FIG. 10B is a cross-sectional view of a capping device.

FIG. 10B shows a representative embodiment of cap device 78 with lid 78a and pad 80. Cap device 78 is a stand-alone device where pad 80 may either be a wet pad or a dry pad. Where pad 80 is a dry pad, cap device 78 is used as described above for cap end 14.

Where pad 80 is a wet pad, cap device 78 may be used to clean access portion A10 of valve A in addition to its capping function. The twisting motion involved in removing and placing cap device 78 with respect to access potion A10 provides friction for cleaning. Additional cleaning can be accomplished by twisting cap device 78 in one direction and then in the reverse direction for a desired amount of time.

Cap device 78 further comprises an inner circumference 82 that defines a cavity in which pad 80 is housed. In some instances, cap device 78 comprises a thread or threading 18 having a length that is less than inner circumference 82.

With either cleaning device 74 or cap device 78, additional gripping surface may be added by extending the length of the housing. The increased gripping surface would provide easier handling of devices 74 and 78.

Cap/cleaner 10 cleans and maintains access valves in antiseptic or aseptic condition. This substantially decreases the risk of patient infections caused by the ingress of microbes into the access valves, particularly for needleless access valves.

Although the present invention has been described with reference to preferred embodiments, workers skilled in the art will recognize that changes may be made in form and detail without departing from the spirit and scope of the invention.

The invention claimed is:

1. A device for cleaning a patient fluid line access valve having an access portion with a distalmost end face and an external thread on at least a portion of an outer surface of a sidewall, the device comprising:
   a housing having an opening with an inner circumference and a maximum inner cross-sectional area greater than a maximum cross-sectional area of the access portion including the external thread, and an inner cavity for receiving the access portion of the patient fluid line access valve via the opening;
   a pad including a cleaning solution;
   an internal threading configured within the inner cavity of the housing to accommodate the external thread of the access portion of the patient fluid line access valve, the access portion providing an access to a fluid line via the access valve when connected to the fluid line, such that a gap providing an air cavity is formed at least between the inner circumference of the opening and the outer surface of the sidewall including the external thread of the access portion of the patient fluid line access valve when the internal threading provides a secured attachment of the cap to the access valve,
   wherein a threading action comprising rotating the housing relative to the patient fluid line access valve causes the external thread and the internal threading to cooperate compressing the pad by the distalmost end face of the access portion of the patient fluid line access valve, thereby allowing the cleaning solution to disinfect at least the distalmost end face of the access portion of the patient fluid line access valve; and
   a removable lid enclosing the inner cavity, the pad and the cleaning solution being in the inner cavity, prior to receiving the access portion of the patient fluid line access valve.

2. The device of claim 1, wherein the threading action between the internal threading and the external thread provides adjustable positioning of the distalmost end face within the inner cavity.

3. The device of claim 2, wherein the adjustable positioning of the distalmost end face within the inner cavity allows at least the distalmost end face to contact and compress the pad at least between the distalmost end face and the inner cavity.

4. The device of claim 1, wherein the pad comprises a sponge.

5. The device of claim 1, wherein the housing comprises a polyethylene or polypropylene material.

6. The device of claim 1, wherein the cleaning solution comprises an antimicrobial agent.

7. The device of claim 6, wherein the antimicrobial agent comprises at least one of chlorhexidine gluconate and chlorhexidine diacetate.

8. The device of claim 6, wherein the cleaning solution is an alcohol-based cleaning solution.

9. The device of claim 1, wherein a thread length of the internal threading is less than an inner circumference of the opening of the housing.

10. The device of claim 9, wherein the gap comprises a void formed by the circumferentially absent thread length of the internal threading.

11. The device of claim 1, wherein the gap extends towards a proximal end of the opening.

12. The device of claim 11, wherein the gap extends to an abutting interface of the patient fluid line access valve and the housing.

13. The device of claim 1, wherein the compressing of the pad by the distalmost end face of the access portion of the patient fluid line access valve allows the cleaning solution to disinfect the outer surface of the sidewall including the external thread of the access portion of the patient fluid line access valve.

14. A method for cleaning a patient fluid line access valve having an access portion with a distalmost end face and an external thread on at least a portion of an outer surface of a sidewall, the method comprising:
   providing a cap having a housing having an opening with an inner circumference and a maximum inner cross-sectional area greater than a maximum cross-sectional area of the access portion including the external thread, an inner cavity for receiving the access portion of the patient fluid line access valve via the opening, the access portion providing an access to a fluid line via the access valve when connected to the fluid line, and an internal threading configured within the opening of the housing;
   removing a removable lid enclosing the inner cavity thereby exposing a pad including a cleaning solution disposed in the inner cavity prior to receiving the access portion of the patient fluid line access valve;

rotating said cap onto the patient fluid line access valve, wherein the internal threading of the cap accommodates the external thread of the access portion of the patient fluid line access valve such that a gap providing an air cavity is formed at least between the inner circumference of the opening and the outer surface of the sidewall including the external thread of the access portion of the patient fluid line access valve when the internal threading provides a secured attachment of the cap to the access valve; and seating said cap onto the patient fluid access valve by a threaded engagement between the internal threading and the external thread thereby forcing the pad to be compressed by the distalmost end face of the access portion of the patient fluid line access valve, thereby allowing the cleaning solution to disinfect at least the distalmost end face of the access portion of the patient fluid line access valve.

15. The method of claim 14, wherein the rotating step further comprises adjusting position of the distalmost end face within the inner cavity by a threaded interaction between the internal threading and the external thread.

16. The method of claim 15, wherein the step of adjusting the position of the distalmost end face within the inner cavity by the threaded interaction comprises the distalmost end face contacting and compressing the pad at least between the distalmost end face and the inner cavity.

17. The method of claim 14, wherein the pad comprises a wetted sponge.

18. The method of claim 14, wherein the cleaning solution comprises an antimicrobial agent.

19. The method of claim 18, wherein the antimicrobial agent comprises at least one of chlorhexidine gluconate and chlorhexidine diacetate.

20. The method of claim 19, wherein the cleaning solution is an alcohol-based cleaning solution.

21. The method of claim 14, wherein the forcing of the pad to be compressed by the distalmost end face of the access portion of the patient fluid line access valve allows the cleaning solution to disinfect the outer surface of the sidewall including the external thread of the access portion of the patient fluid line access valve.

* * * * *